(12) United States Patent
Clendennen et al.

(10) Patent No.: US 6,720,476 B2
(45) Date of Patent: Apr. 13, 2004

(54) CTR1 HOMOLOGUE FROM MELON

(75) Inventors: Stephanie K. Clendennen, Portland, OR (US); Debra K. Schuster, Portland, OR (US)

(73) Assignee: Exelixis Plant Sciences, Inc., Portland, OR (US)

( * ) Notice: Subject to any disclaimer, the term of this patent is extended or adjusted under 35 U.S.C. 154(b) by 0 days.

(21) Appl. No.: 09/904,389

(22) Filed: Jul. 12, 2001

(65) Prior Publication Data

US 2002/0129404 A1 Sep. 12, 2002

Related U.S. Application Data

(60) Provisional application No. 60/218,307, filed on Jul. 14, 2000.

(51) Int. Cl.[7] ........................ C12N 15/82; C12N 15/29; C12N 1/21; C12N 15/10; A01H 5/00
(52) U.S. Cl. ........................ 800/283; 800/298; 536/23.6; 435/252.3; 435/320.1; 435/419
(58) Field of Search .............................. 435/320.1, 419, 435/468, 252.3; 536/23.6; 800/283, 290, 298

(56) References Cited

U.S. PATENT DOCUMENTS 5,602,322 A 2/1997 Ecker et al.

OTHER PUBLICATIONS

Rhoads et al. Regulation of the cyanide–resistant alternative oxidase of plant mitochondria. J. Biol. Chem., Nov. 1998, Vo 273, No. 46, pp. 30750–30756.*

Kieber, et al., *Cell* 72:427–411, (1993).

* cited by examiner

*Primary Examiner*—David T. Fox
*Assistant Examiner*—Cynthia Collins
(74) *Attorney, Agent, or Firm*—Perkins Coie LLP

(57) ABSTRACT

The invention relates to the nucleic acid and amino acid sequences for a melon constitutive triple response (CTR1) homologue, called mCTR, vectors, cells and transgenic plants which comprise the coding sequence for mCTR or a biologically active fragment thereof and methods of producing transgenic plants which express mCTR or a biologically active fragment thereof.

12 Claims, 5 Drawing Sheets

Fig. 1A

```
TCAAGTTTTTGTCAACGGATGGGAAGTGTTGGAAAACTTCAACTGCTAGACGATTCCATCA
AATTTATTCTCACTTCATAATCATCAAAATCTAGAGAGATTATAAAAATGTGGATCACTTCA
TAGTCCACAATCAAGGAAGTTTCTACCTTTTTGCTATGGTGATGAAGAAACTTCAACTCCAT
GTCACCCTATTTCACTTCACACATTATTTGTTTGTATATCTATTGGTCTTACCTTTGACGAC
CGGACCAGGAACTAATTTTGTATATACTAGTGATCAGTTGTGGATGGATGCAATCATGTCTT
CAGTCAGACTTGGTGTTTGCTAGGGAAATATCATTGTTGTTATTAACAGCCACTTCAAACA
TTCAATTAATTTTCACCCAGTCTATTATTCTAAAAAAAAAAAAAAAAAAAAAAAAA
```

Fig. 1B

```
MEMPGFRSDYSLLSQIPDEEVGTGASTSFYDSVAAGNVIKGRTDFVFDWCGSGDHRLNTQA
YRTGNLYSWIGLQRHSSGSSYDDSSLSSDYYAPTLSNPAANEINALEYILDDFRVMKAVGS
GGSSGFSWAQDTEESFQLQQPLVLFLSSDKTCADDPNFMDPIPDEAALRSISISAEAISHRF
WVNGCMSYLEKVPDGFYLIHGMDPYVWSLCTNLQEDGRIPSFESLKTVDSSIGSSIEVVLID
RHSDASLKELQNFVHNISSSCVTTHEVADHIAKLVCNHLGGSVSEGEDDLVSAWKECSDDLK
ECLGSAVIPLCSLSVGLCRHRALLFKVLADSIDLPCRIAKGCKYCTRDDASSCLVRFGLDRE
YLIDLTGRPGCLCQPDSLLNGPSSISISSPLRFPRLKPIESTIDFRSLAKQYFLDSQSLNLV
FDEASSGNVVSGKDAAFSVYQRPLNRKDVDGKTIVVTGDKDRNSQLLNKKAAQLNTQDGKSE
QFFSCVASPYSVQSTPFVENVVPLSHISHIGSEDSEHLLALSHPRMDHVNNLPFVHGSQLIR
KPNELSLGLEDLVIPWTDLDLREKIGAGSFGTVYRGEWHGSDVAVKILTEQDFHPERVNEFL
REVATMKSLRHENIVLFMGAVTKPPNLSIVTEYLSRGSLYRLLHKSGVKDIDETRRINMAFD
VAKGMNYLHRRDPPIVHRDLKSPNLLVDKKYTVKVCDFGLSRLKARTFLSSKSAAGTPEWMA
PEVLRDEPSNEKSDVYSFGVILWELATLQQPWCNLNPAQVVAAVGFKGKRLDIPRDVNPKLA
SLIVACWADEPWKRPSFSSIMETLKPMTKDAPPQQSRTDTLSVM
```

Fig. 2

A= actin ; C= melonCTR

CTR1 HOMOLOGUE FROM MELON

This application claims priority to U.S. Provisional Application Serial No. 60/218,307, Filed on Jul. 14, 2000 expressly incorporated by reference herein.

FIELD OF THE INVENTION

The invention is concerned with a melon constitutive triple response (CTR1) homologue, called mCTR, vectors, cells and transgenic plants which comprise the coding sequence for mCTR or a biologically active fragment thereof and methods of producing transgenic plants which express mCTR or a biologically active fragment thereof.

REFERENCES

Alonso, J M et al., Science. 284: 2148–52, 1999.
Altschul et al., Nucl. Acids Res. 25(17) 3389–3402, 1997.
An, G. et al., EMBO J. 4:277–284, 1985.
Ayub, R. et al., Nature Biotechnology 14:862–866, 1996.
Beck E et al, Gene 19: 327–36, 1982.
Becker D et al, Plant Mol Biol 20: 1195–7, 1992.
Bellini, C. et al., Bio/Technology 7(5):503–508, 1989.
Bleecker, A. B. and G. E. Schaller, Plant Physiol. 111: 653–60, 1996.
Carter et al, Nucl. Acids Res. 13:4331, 1986.
Chang C et al., In: BIOLOGY AND BIOTECHNOLOGY OF THE PLANT HORMONE ETHYLENE II, Kanellis et al. Eds. Kluwer, Boston. p. 65–70,
Chao, Q et al., Cell, 89: 1133–44, 1997.
Clark, K L et al., Proc. Natl. Acad. Sci USA 95: 5401–6, 1998.
Comai, L. and Coning, A. J., U.S. Pat. No. 5,187,267, issued Feb. 16, 1993.
Crameri A and Stemmer W P, Bio Techniques 18(2):194–6, 1995.
Creighton, T. E., PROTEINS: STRUCTURE AND MOLECULAR PROPERTIES, W. H. Freeman & Co., San Francisco, pp. 79–86,1983.
Deikman, J., et al., EMBO J. 7:3315 (1988).
Deikman, J. et al., Plant Physiol. 100(4):2013–2017, 1992.
Depicker, A., et al., J. Mol. Appl. Genet. 1:561–573, 1982.
Dong, J. Z. et al., Bio/Technology 9:858–863, 1991.
Doolittle, R. F., OF URFS and ORFS, University Science Books, CA, 1986.
Fang, G. and Grumet, R., Plant Cell Rep. 9:160–164, 1990.
Fils-Lycaon et al., Plant Physiol 111:269–273, 1996.
Glick, B. R. and Thompson, J. E., Eds. METHODS IN PLANT MOLECULAR BIOLOGY AND BIOTECHNOLOGY, p. 213–221, CRC Press, 1993.
Gonsalves, C. et al., J. Amer. Soc. Hort. Sci. 119:345–355, 1994.
Hajdukiewicz P et al., Plant Mol Biol 25: 989–94, 1994.
Harlow and Lane, Antibodies, A Laboratory Manual, Cold Spring Harbor, 1988.
Haught C et al., BioTechniques 16(1):47–48, 1994.
Hopp et al., Biotechnology 6: 1204–1210, 1988.
Hua J and Meyerowitz E M. Cell, 94: 261–271, 1998.
Huang et al., abstract S09–30, 6th International Congress of Plant Molecular Biology, Quebec, Canada, 2000.
Hughes, J. A. et al., J. Bact. 169:3625–3632, 1987a.
Hughes, J. A., et al., Nuc. Acid. Res. 15:717–729, 1987b.
Kieber, J. J. et al., Cell 72: 427–41, 1993.
Kieber, J. J, J. Exper. Botany 48: 211–8, 1997.
Klein, T. M. et al., PNAS USA 85(22):8502–8505, 1988.
Kunkel T A et al., Methods Enzymol. 204:125–39, 1991.
Maniatis, T. et al., in Molecular Cloning: A Laboratory Manual, Cold Spring Harbor Laboratory, Cold Spring Harbor, N.Y., 1989.
McCormick et al., Plant Cell Reports 5:81–84, 1986.
Mertens, et al. Virology 131(1):18–29, 1983.
Miki, B. L. A. et al, Plant DNA Infectious Agents (Hohn, T. et al., Eds.) Springer-Verlag, Vienna, Austria, pp. 249–265, 1987.
Nagel, R., et al., FEMS Microbiol. Lett. 67:325, 1990.
Norelli et al., HortScience 31:1026–1027, 1996.
Oh, S. A. et al., Plant J. 12: 527–35, 1997.
Payton, S. et al., Plant Mol. Biol. 31: 1227–31, 1996.
Ranier et al., Bio/Technology 8:33–38, 1990.
Robinson, H. L. and Torres, C. A., Sem. Immunol. 9:271–282, 1997.
Sagi et al., Bio/Technology 5:481–485, 1995.
Sambrook et al., Molecular Cloning: A Laboratory Manual (Second Edition), Cold Spring Harbor Press, Plainview, N.Y.,1989.
Satoh S et al., In: BIOLOGY AND BIOTECHNOLOGY OF THE PLANT HORMONE ETHYLENE II, Kanellis et al. Eds. Kluwer, Boston. p. 441–442, 1999.
Schwarz-Sommer, et al., EMBO J. 11(1):251–63, 1992.
Sisler E C and Blankenship S M. Plant Growth Regulation 12: 125–32, 1993.
Sisler E C and Serek M, In: BIOLOGY AND BIOTECHNOLOGY OF THE PLANT HORMONE ETHYLENE II, Kanellis et al. Eds. Kluwer, Boston. Pp. 45–50, 1999.
Solano, R et al., Curr Opin Plant Biol 1(5):393–398, 1998.
Studier, F. W. et al., J. Virol 19:136–145, 1976.
Tieman D M et al., Proc Natl Acad Sci USA 97: 5663–8, 2000.
Valles, M. P. and Lasa, J. M., Plant Cell Rep. 13:145–148, 1994.
Velten J et al., J. Nucleic Acids Res 13(19):6981–98, 1985.
Verdaguer, B., et al., Plant Mol Biol 31: 1129–1139, 1996.
Wang, Y. and N. Li, Plant Physiol. 114: 1135, 1997.
Wells et al., Gene 34:315, 1985.
Wells et al., Philos. Trans. R. Soc. London SerA 317:415, 1986.
Woeste, K et al., Trans R. Soc. Lond. B. Biol Sci 29:353 (1374)1431–1438, 1998.
Woeste K E and Kieber J J. In: BIOLOGY AND BIOTECHNOLOGY OF THE PLANT HORMONE ETHYLENE II, Kanellis et al. Eds. Kluwer, Boston. p. 37–43, 1999.
Xu, R. et al., Plant Mol. Biol. 31:1117–1127, 1996.
Yamada et al., Plant Cell Physiol 40:198–204, 1999.
Yoshioka, K. et al., Jpn. J. Breeding 42(2):278–285, 1992.
Zoller et al., Nucl. Acids Res. 10:6487, 1987

BACKGROUND OF THE INVENTION

Ethylene ($CH_2=CH_2$), is a naturally occurring plant hormone which has diverse effects on plant growth and development when produced by the plant itself or applied exogenously. Ethylene promotes senescence in plants, both in selected groups of cells and in whole organs such as fruits, leaves and flowers. Ethylene mediated effects, such as the stimulation of ripening in fruits and vegetables; leaf abscission, yellowing and epinasty, and fading and wilting in flowers are of considerable commercial importance to fruit, vegetable and flower-related industries. Large quantities of ethylene are produced by plants during ripening and senescence and in response to trauma caused by chemicals, temperature extremes, water stress, ultraviolet light, insect damage, disease and mechanical wounding.

Reducing ethylene biosynthesis is an effective way of prolonging the ripening process in fruit and also has potential to delay post harvest senescence. An alternative to reducing ethylene biosynthesis is to reduce the plant's ability to perceive and respond to ethylene by interfering with the signal transduction pathway leading to the ethylene response. A plant's ability to respond to ethylene is correlated with transcription of ethylene perception pathway components (Payton et al., 1996), and mutant plants insensitive to ethylene show a delayed senescence phenotype (Oh et al. 1997; Chao et al. 1997). Great strides have been made in elucidating the signal transduction cascade responsible for ethylene perception in plants.

The ethylene receptor and downstream components of the ethylene perception pathway have been identified, and in some plant species the corresponding genes have been cloned. In Arabidopsis, the ethylene receptor is a member of an extended gene family which includes ETR1, ERS1, ERS2, ETR2, and EIN4 (Hua et al., 1998). Mutations at these loci result in plants that are insensitive to ethylene, and the mutations studied to date have been dominant.

A need exists for further elucidating the effects of blocking the ethylene response on fruit, vegetable and flower development and for modulating the ethylene response in a variety of agricultural industries.

SUMMARY OF THE INVENTION

It is a general object of the invention to provide methods for interference with ethylene perception and ethylene response in the fruit of fruit-bearing plants.

The invention provides an isolated nucleic acid molecule comprising a nucleic acid sequence encoding a melon protein with the activity of a constitutive triple response (CTR) protein, wherein the nucleic acid sequence is selected from the group consisting of:

(a) a nucleic acid sequence encoding a protein comprising the amino acid sequence of SEQ ID NO: 2;

(b) a nucleic acid sequence that is SEQ ID NO: 1;

(c) a nucleic acid sequence that is nucleotides A-3286 of SEQ ID NO:1, wherein A is any one of nucleotides 1440–1444;

(d) a nucleic acid sequence that has at least 80, 85 or 90% sequence identity to the coding region of (a), (b) or (c)

(e) a nucleic acid sequence that will hybridize under moderate to high stringency conditions to the sequence presented as SEQ ID NO:1, or the complement thereof;

(f) a fragment of the nucleic acid sequence of (a), (b) or (c) wherein the fragment encodes a protein which has the activity of a constitutive triple response (CTR) protein; and (g) a nucleic acid sequence that is degenerate as a result of the genetic code to the nucleic acid sequence of (a), (b), (c), (d), (e) or (f).

In a related aspect, the invention provides a plant expression vector comprising an mCTR nucleic acid sequence selected from those described above, operably linked to control sequences recognized by a plant cell transformed with the vector and transgenic plant cells comprising the nucleic acid sequence or plant expression vector.

The invention also provides mature transgenic plants comprising such transgenic plant cells.

In a further related aspect, the invention provides an isolated protein having the activity of a constitutive triple response (CTR) protein, wherein the protein is encoded by a nucleic acid sequence selected from those described above.

A method for producing transgenic plant lines having a decreased response to ethylene is also provided by the invention. The method includes the steps of introducing a plant expression vector, comprising an mCTR nucleic acid sequence selected from those described above, into cells of a plant under conditions effective to yield transformed plant cells, selecting for transformed plant cells and growing the selected plant cells to produce a transgenic plant line, the seedlings of which exhibit a modulated triple response to ethylene.

These and other objects and features of the invention will be more fully appreciated when the following detailed description of the invention is read in conjunction with the accompanying drawings.

BRIEF DESCRIPTION OF THE FIGURES

FIGS. 1A and B depict the 3286 nucleotide sequence of the *Cucumis melo* CTR1 homologue (mCTR).

FIG. 2 depicts the deduced amino acid sequence for the *Cucumis melo* CTR1 homologue (mCTR; 850 amino acids).

DETAILED DESCRIPTION OF THE INVENTION

I. Definitions

Figure 3:
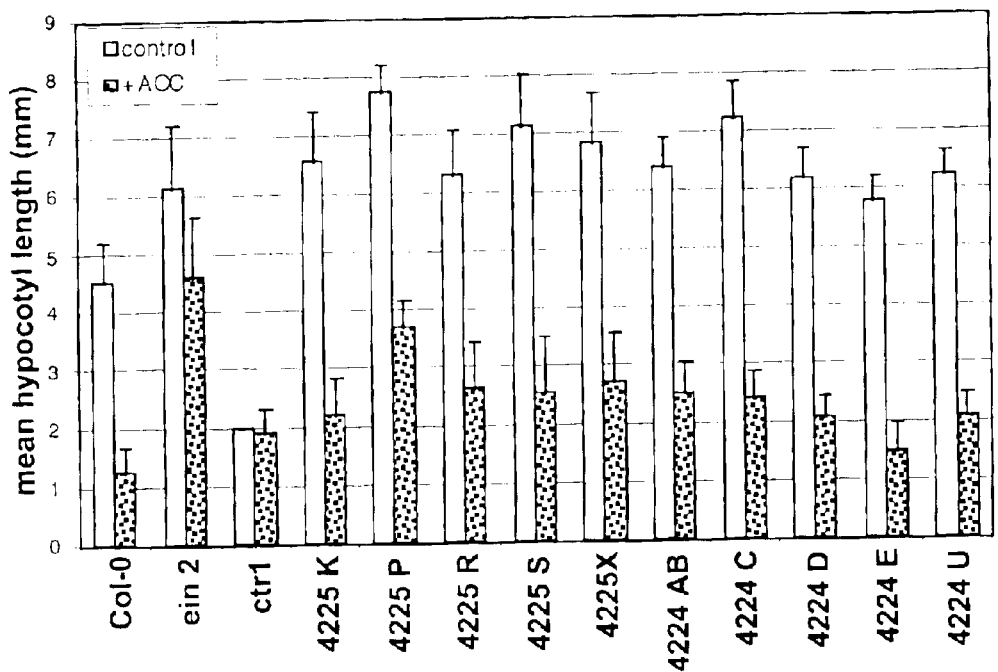
FIG. 3 shows the results of an assay for hypocotyl length as an indicator of the triple response in Arabidopsis seedlings germinated on solid nutrient medium or on the same medium supplemented with 100 $\mu$M ACC. The hypocotyl length of at least 20 seedlings per line was measured to the nearest mm. The mean hypocotyl length (+SD) of untransformed Arabidopsis (Col-0), the two ethylene response mutants (ein 2 and ctr1), and 5 independent transformation events for the pAG4224 and pAG4225 mCTR expression constructs is shown in the figure.

The terms below, have the following meanings, unless otherwise indicated:

As used herein, the term "polynucleotide" refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded ribonucleic acids (RNA) and deoxyribonucleic acids (DNA), and may include polymers having backbone modifications such methylphosphonate linkages.

A nucleic acid may be double stranded, single stranded, or contain portions of both double stranded and single stranded sequence. The depiction of a single strand also defines the sequence of the other strand and thus also includes the complement of the sequence which is depicted.

As used herein, the term "recombinant nucleic acid" refers to a nucleic acid, originally formed in vitro, in general, by the manipulation of the nucleic acid using endonucleases, in a form not normally found in nature.

As used herein, the terms "chimeric gene", "chimeric gene construct" and "chimeric nucleic acid construct" are used interchangeably and refer to recombinant nucleic acid sequences which comprise a DNA coding sequence and control sequences required for expression of the coding sequence in a plant cell.

As used herein, the term "ethylene regulated", refers to regulation which is induced by changes in ethylene concentration in the plant. For example, promoter activity which occurs or primarily occurs, during later stages of fruit development and/or early stages of fruit ripening, is said to be ethylene regulated.

As used herein, the term "ethylene response" refers to a biochemical, physiological, molecular or morphological effect of ethylene. Morphological changes include the triple response in seedlings and a compact stature in adult plants. Physiological responses to ethylene include, but are not limited to a delay in senescence and fruit ripening or alterations in ethylene-related defense and stress responses. Biochemical changes include, but are not limited to auto-catalytic alterations in ethylene production. Molecular responses include, but are not limited to an alteration in the expression of ethylene-induced genes such as those encoding chitinase B and ERF1, or in the activity of ethylene-associated promoters such as E8 and E4 from tomato.

As used herein, the term "ethylene perception pathway" refers to the biochemical or genetic components involved in the ethylene signal transduction pathway leading to an ethylene response in plants.

As used herein, the term "modified ethylene response phenotype" refers to a modification made to an ethylene response as a result of the genetic manipulation of a plant or plant cell.

As used herein, the term "transgene", refers to a non-native nucleic acid sequence, usually encoding a polypeptide, introduced into a host genome using recombinant DNA techniques.

As used herein, the term "regulatable promoter" refers to any promoter whose activity is affected by specific environmental or developmental conditions (e.g., a tomato E4 or E8 promoter).

As used herein, the term "constitutive promoter" refers to any promoter that directs RNA production in many or all tissues of a plant transformant at most or all times.

As used herein, the term "tissue-associated promoter" refers to any promoter which directs RNA synthesis at higher levels in particular types of cells and tissues, e.g., an apple fruit-associated promoter directs RNA synthesis at higher levels in apple fruit, relative to expression levels in apple leaves.

As used herein, the terms "promoter" or "promoter segment" refer to a sequence of DNA that functions in a promoter disclosed herein to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid coding sequence is "heterologous" with respect to a control sequence (i.e. promoter or enhancer) when the control sequence does not function in nature to regulate the same gene the expression of which it is currently regulating. Generally, heterologous nucleic acid constructs are introduced into the cell or part of the genome in which they are present, and have been added to the cell, by transfection, microinjection, electroporation, or the like. Although the control sequence or the nucleic acid coding sequence may be found in nature, the sequences represent a control sequence/coding sequence combination that is different from a control sequence/coding sequence combination found in the native plant.

As used herein, the term "operably linked" relative to a nucleic acid component of a chimeric or heterologous nucleic acid construct or vector means the nucleic acid component is in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

As used herein, the term "plasmid" refers to a circular double-stranded (ds) DNA construct used as a cloning vector, and which forms an extrachromosomal self-replicating genetic element in many bacteria and some eukaryotes.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons). The term "gene", may be used interchangeably herein with the term "nucleic acid coding sequence", and the term "structural gene" which means a DNA coding region.

As used herein, the term "mCTR coding sequence" refers to a nucleic acid sequence (DNA, or RNA) which encodes a melon mCTR gene product that functions in the ethylene response pathway in plants. Such an mCTR coding sequence may be the full length coding sequence or a fragment, variant or modified (e.g., epitope-tagged) form thereof, where the sequence encodes an mCTR gene product that exhibits an activity of a constitutive triple response (CTR) protein.

Amino acid residues are referred to herein by their standard single letter notations: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; Y, tyrosine.

The term "polypeptide" as used herein refers to a compound made up of a single chain of amino acid residues linked by peptide bonds. The term "protein" as used herein may be synonymous with the term "polypeptide" or may refer, in addition, to a complex of two or more polypeptides. In the context of the present invention, a "protein complex" refers to multiple copies of the same protein or protein fragment that bind to a single ribonucleotide fragment.

Generally, but not always, polypeptides and proteins are formed predominantly of naturally occurring amino acids.

As used herein, the term "sequence identity" means nucleic acid or amino acid sequence identity in two or more aligned sequences, aligned using a sequence alignment program. Sequence searches are preferably carried out using the BLASTN program when evaluating the of a given nucleic acid sequence relative to nucleic acid sequences in the GenBank DNA Sequences and other public databases. The BLASTX program is preferred for searching nucleic acid sequences which have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (Altschul et al., 1997)

The term "% homology" is used interchangeably herein with the term "% identity" herein and refers to the level of identity between two sequences, i.e. 80% homology means the same thing as 80% sequence identity as determined by a defined algorithm, and accordingly a homologue of a given sequence has at least about 85%, 90% or greater sequence identity over a length of the given sequence.

A preferred alignment of selected sequences in order to determine "% identity" between two or more sequences, is performed using the CLUSTAL-W program in MacVector version 6.5, operated with default parameters, including an open gap penalty of 10.0, an extended gap penalty of 0.1, and a BLOSUM 30 similarity matrix.

A nucleic acid sequence is considered to be "selectively hybridizable" to a reference nucleic acid sequence if the two sequences specifically hybridize to one another under moderate to high stringency hybridization and wash conditions. Exemplary conditions include hybridization conducted as described in the Bio-Rad Labs ZetaProbe manual (Bio-Rad Labs, Hercules, Calif.), expressly incorporated by reference herein. For example, hybridization is conducted in 1 mM EDTA, 0.25 M $Na_2HPO_4$ and 7% SDS at 60° C., followed by washing in 1 mM EDTA, 40 mM $NaPO_4$, 5% SDS, and 1 mM EDTA, 40 mM $NaPO_4$, 1% SDS. Hybridization conditions are further recited in Ausubel F M et al., 1993, expressly incorporated by reference herein.

As used herein, the term "expression" refers to the process by which a polypeptide is produced based on the nucleic acid sequence of a gene. The process generally refers to both transcription and translation.

As used herein, the terms "transformed", "stably transformed" or "transgenic" with reference to a plant cell means the plant cell has a non-native (heterologous) nucleic acid sequence integrated into its genome which is maintained through two or more generations.

Generally, a "variant" polynucleotide sequence encodes a "variant" amino acid sequence which is altered by one or more amino acids from the reference polypeptide sequence. The variant polynucleotide sequence may encode a variant amino acid sequence having "conservative" or "non-conservative" substitutions. Variant polynucleotides may also encode variant amino acid sequences having amino acid insertions or deletions, or both. Variant mCTR coding sequences that encode a gene product which exhibits the activity of a constitutive triple response (CTR) protein are within the scope of the present invention. with the activity of a constitutive triple response (CTR) protein.

As used herein, the term "modulate" refers to a change in biological activity. Modulation may relate to an increase or a decrease in biological activity, binding characteristics, or any other biological, functional, or immunological property of the molecule.

As used herein, a "plant cell" refers to any cell derived from a plant, including undifferentiated tissue (e.g., callus) as well as plant seeds, pollen, progagules and embryos.

As used herein, the term "mature plant" refers to a fully differentiated plant.

As used herein, the terms "native" and "wild-type" relative to a given plant trait or phenotype refers to the form in which that trait or phenotype is found in the same variety of plant in nature.

II. Ethylene Regulation in Plants

The present invention is directed to blocking or delaying undesirable ethylene-mediated responses including fruit ripening, flower senescence and abscission.

It been observed that genes which encode a number of proteins typically induced by pathogens can be transcriptionally activated by ethylene and their expression blocked by inhibitors of ethylene biosynthesis.

The ethylene biosynthetic pathway includes an ethylene biosynthesis and an ethylene autoregulatory or feedback component. In the biosynthetic pathway leading to ethylene, methionine is converted to ethylene with S-adenosylmethionine (SAM) and 1-aminocyclopropane-1-carboxylic acid (ACC) as intermediates. These two reactions are catalyzed by ACC synthase and ethylene-forming enzyme (EFE), respectively.

An enzyme encoded by the *E. coli* bacteriophage T3 hydrolyzes AdoMet to homoserine and 5'-methylthioadenosine (MTA). The enzyme is known as AdoMet hydrolase (AdoMetase), or as S-adenosylmethionine cleaving enzyme (SAMase) (Studier et al., 1976; Hughes et al., 1987a; Hughes et al., 1987b). Other bacteriophages that encode the AdoMetase or SAMase genes are coliphage BA14, Klebsiella phage K11, and Serratia phage IV (Mertens et al. 1983).

There are numerous examples of blocking ethylene production as a means to modify the effects of ethylene on fruits, vegetables and flowers. For example, inhibitors of ethylene biosynthesis such as AVG and silver thiosulfate (STS) have been commonly used as research tools to study ethylene-mediated responses in plants and practically as anti-senescence preservatives for cut flowers. However, their toxicity makes them unattractive for use with edible plant tissues. A novel compound, 1,1-dimethyl-4-(phenylsulfonyl) semicarbazide (DPSS), has a similar ethylene blocking action and has been suggested as a less toxic alternative (Satoh et al. 1999).

Compounds that block ethylene perception are valuable research tools and may be effective at reducing the detrimental effects of ethylene, especially during post-harvest storage of fruits and vegetables. Diazocyclopentadiene (DACP) is structurally related to cyclopentadiene, an effective blocking agent (antagonist) for ethylene binding to the receptor (Sisler et al. 1993). DACP interacts with the ethylene receptor and can be "permanently" bound under low illumination to inactivate most physiological activity of ethylene. 2,5-Norbornadiene (2,5-NBD) is also an ethylene antagonist, but its action requires continuous exposure. 1-Methylcyclopropene (1-MCP) is another effective ethylene antagonist with the advantage that a single exposure results in a long-lasting inhibitory effect (Sisler et al., 1999).

The ethylene response pathway has been studied genetically in Arabidopsis by screening for mutants impaired in typical ethylene responses. The response of a normal dark-grown seedlings to ethylene to the production or administration of ethylene, has been designated the "triple response". At the seedling stage, the triple response is often used as an indicator of ethylene response, namely a radial swelling of the hypocotyl, exaggeration of the apical hook, and inhibition of root and hypocotyl elongation in the dark. (See, e.g., Solano et al., 1998; and Woeste et al., 1998.) In the continuous presence of ethylene, adult plants also show a typical ethylene response phenotype, including a compact morphology and constitutive expression of ethylene-induced genes such as chitinase B. Screens for ethylene perception alterations may be devised to identify mutants that are either insensitive to ethylene or that show a constitutive ethylene response even in the absence of the hormone.

Components of the ethylene perception pathway were first identified as ethylene response mutants in Arabidopsis (reviewed in Kieber, 1997; Bleecker et al., 1996). In Arabidopsis, the ethylene receptor is a member of an extended gene family which includes ETR1, ERS1, ERS2, ETR2, and EIN4 (Hua et al., 1998). Detailed genetic studies have revealed that the ethylene receptor family negatively regulates ethylene responses (Hua et al., 1998). Other ethylene insensitive Arabidopsis mutants which have been identified include, ein2 and ein3, and both corresponding genes have been shown to be positive regulators of the ethylene response pathway. The overexpression of positive regulators of the ethylene response pathway such as EIN2 and EIN3 has been shown to lead to a constitutive ethylene response phenotype. EIN2 has been isolated and shown to act downstream of CTR1. EIN2 encodes an integral membrane protein that functions in both ethylene perception and stress responses (Alonso et al., 1999). Overexpression of the full-length EIN2 protein or N-terminal region does not result in a constitutive ethylene response, but expression of the C-terminal domain alone was shown to result in a CTR1-like phenotype. It has been demonstrated that EIN3 encodes a nuclear-localized protein, and that overexpression of EIN3 also confers constitutive ethylene responses (Chao et al., 1997).

Mutants that show a constitutive ethylene response include those that overproduce ethylene (eto1, eto2, eto3; Woeste et al., 1999) or constitutively activate the ethylene response pathway, such as ctr1 from Arabidopsis. Because the ctr1 null mutant has been observed to exhibit a constitutive ethylene response even in the absence of ethylene, CTR1 has been implicated as a negative regulator of ethylene perception (Kieber et al. 1993; Kieber, 1997). The deduced amino acid sequence of the wild-type CTR1 from Arabidopsis shares homology with the Raf family of Ser/Thr kinases. Kinase activity has been demonstrated for CTR1 and is believed to be required for its activity in vivo.

The constitutive triple response gene (CTR1) from Arabidopsis is the subject of U.S. Pat. Nos. 5, 367,065; 5,444, 166 and 5,602,322. Following isolation of the gene encoding CTR1 from Arabidopsis (GenBank Accession No. L08789), other CTR1-like homologues have been identified. A full-length cDNA sequence of a CTR1 homologue from tomato has been reported (Wang et al., 1997; GenBank Accession No. Y13272), as well as CTR1-like fragments from large-scale EST analyses of immature rice seed (GenBank Accession No. AA752333) and mature sugarcane stalk (GenBank Accession No. AA644724).

The full length CTR1 cDNA sequences from Arabidopsis and tomato are each approximately 3 kb in length and show some homology at regions throughout the sequence, but especially at the 5' end 3' ends, the latter of which encodes the kinase domain. Based on its deduced amino acid sequence, mCTR is a protein with two functional domains. The C-terminal domain shares significant sequence similarity to protein kinases, while the N-terminal domain may function to regulate the kinase activity of the protein. The regulatory role of the N-terminal domain has not been characterized.

Multiple mutant analysis has suggested that CTR1 acts downstream of the ethylene receptor(s) and interacts with both ETR1 and ERS1 (Clark et al., 1998; Chang et al., 1999). While the mechanism is not part of the discovery, it has been shown via yeast two-hybrid assays that CTR1 interacts directly with the ethylene receptor. The in vitro interaction occurs between the N-terminal "regulatory" domain of CTR1 and the C-terminal histidine kinase domain of both ETR1 and ERS. In the absence of ethylene, the interaction between CTR1 and the ethylene receptor(s) is thought to activate CTR1 and repress ethylene responses. Ethylene binding to the receptors inhibits their signaling/activation of CTR1 and the ethylene response is de-repressed (Hua et al., 1998). A similar model of ethylene receptor action has also been proposed for tomato (Tieman et al., 2000). It has been postulated that ethylene binding to the receptor inactivates the kinase activity of CTR1, which ultimately leads to changes in ethylene-regulated gene expression (Kieber, 1997). Therefore, overexpression of CTR1, either the full-length coding region or a fragment that includes the kinase region, may serve to render a plant insensitive to ethylene, if the overexpressed kinase remains active as a negative regulator of the ethylene signaling pathway. Alternatively, in the absence of this interaction, the N-terminal region of CTR1 itself may serve to negatively regulate the activity of the CTR1 kinase domain. If this model is correct, the full-length CTR1 protein alone might be inactive in regulating the ethylene response pathway, and regulation may require independent expression of the kinase domain of CTR1 to obtain the desired activity.

III. Compositions and Methods of the Invention

A. mCTR Nucleic Acid and Amino Acid Sequences

The invention provides the nucleic acid sequence (SEQ ID NO:1) and deduced amino acid sequence (SEQ ID NO:2) for melon mCTR and a biologically active fragment thereof. By biologically active fragment is meant a fragment of a mCTR nucleic acid or protein which exhibits a biological activity typically exhibited by the corresponding full length mCTR nucleic acid or protein sequence in the ethylene response pathway in a plant, e.g., negative regulation of ethylene perception. The biological activity may be of the same or different magnitude relative to the activity of a full-length mCTR nucleic acid or protein.

The mCTR nucleic acid sequence of the invention was isolated by performing the steps of (1) amplifying the 5' and 3' ends of a CTR1 homologue from a PCR-accessible cDNA library from ripe melon fruit using degenerate primers; (2) performing 5' RACE PCR to obtain the response regulator region of the CTR1 homologue; (3) performing 3' RACE PCR to obtain the kinase domain of the CTR1 homologue; (4) using a specific primers from the RACE products to amplify an internal variable region of the melon CTR1 homologue; (5) ligating the 3 fragments together and inserting them into a cloning vector; and (6) adding an epitope tag to monitor expression.

In one embodiment, the invention provides an isolated nucleic acid molecule comprising a nucleic acid sequence encoding a melon protein with the activity of a constitutive triple response (CTR) protein, wherein the nucleic acid sequence is selected from the following:

(a) a nucleic acid sequence encoding a protein comprising the amino acid sequence of SEQ ID NO: 2;

(b) a nucleic acid sequence that is SEQ ID NO: 1;

(c) a nucleic acid sequence that is nucleotides A-3286 of SEQ ID NO:1, wherein A is any one of nucleotides 1440–1444;

(d) a nucleic acid sequence that has at least 85 to 90 or 95% sequence identity to the coding region of (a), (b) or (c);

(e) a fragment of the nucleic acid sequence of (a), (b) or (c) wherein the fragment encodes a protein which has the activity of a constitutive triple response (CTR) protein; and (f) a nucleic acid sequence that is degenerate as a result of the genetic code to the nucleic acid sequence of (a), (b), (c), (d) or (e).

In another embodiment, the invention provides a melon mCTR protein or polypeptide amino acid sequence which has at least about 85% and preferably greater than about 90% or 95% sequence identity to the amino acid sequence presented as SEQ ID NO:2. In related embodiments, the invention provides the nucleotide sequence encoding such a melon mCTR protein or polypeptide, a mCTR protein encoded by a nucleic acid sequence selected from the following:

(a) the nucleic acid sequence presented as SEQ ID NO: 1;

(b) the nucleic acid sequence presented as nucleotides A-3286 of SEQ ID NO:1, wherein A is any one of nucleotides 1440–1444;

(c) a nucleic acid sequence that has at least 85 to 90 or 95% sequence identity to the coding region of (a) or (b);

(d) a fragment of the nucleic acid sequence of (a) or (b) wherein the fragment encodes a protein which has the activity of a constitutive triple response (CTR) protein; and (e) a nucleic acid sequence that is degenerate as a result of the genetic code to the nucleic acid sequence of (a), (b), (c) or (d).

In another related aspect, the invention provides polynucleotide sequences encoding a melon mCTR protein or polypeptide wherein the polynucleotide sequence has greater than about 90% or 95% sequence identity to the melon mCTR protein or polypeptide coding sequence presented as SEQ ID NO:1.

In a further related aspect, a melon mCTR protein or polypeptide coding sequence of the invention will hybridize under moderate to high stringency conditions to a sequence presented as SEQ ID NO:1, or the complement thereof.

The invention also provides vectors comprising a nucleic acid sequence encoding a melon mCTR protein or polypeptide (as described above), operably linked to regulatory elements effective for expression in a plant cell.

A Basic BLASTN search of non-redundant nucleic acid sequence databases through NCBI was conducted on May 25, 2000 using the search capabilities of the NIH website with the nucleotide sequence presented in FIGS. 1A–1B (mCTR, a melon CTR1 homologue nucleic acid sequence). A Basic BLASTP search of non-redundant SwissProt sequences was also conducted on May 25, 2000 through NCBI using the search capabilities of the NIH website with the amino acid sequence presented in FIG. 2. The results of the searches indicated that when compared to Arabidopsis CTR1, the melon mCTR sequence is 58% identical at the nucleotide level and 62% identical at the amino acid level. When compared to tomato CTR1, the melon mCTR sequence is 57% identical at the nucleotide level and 58% identical at the amino acid level. In addition, the melon sequence shows significant conservation in the putative kinase encoding region, suggesting that the cDNA is likely to encode a protein with kinase activity in melon.

The Arabidopsis CTR1 kinase domain was identified as extending from amino acid 551 to the end (821 amino acids; Kieber et al., 1993). The kinase activity of this fragment has been confirmed in vitro (Huang et al., 2000).

In one aspect, the invention provides an amino acid and nucleic acid sequence which includes the predicted kinase domain of the melon CTR homologue (the region extending from amino acid 577 to 850 in the deduced amino acid sequence and nucleotide 1861 to 2682 in the melon CTR cDNA sequence, respectively). This kinase region is 81% conserved between the melon and Arabidopsis sequence at the amino acid level.

The invention provides isolated nucleic acid sequences comprising a nucleic acid sequence which encodes or is complementary to a sequence which encodes a melon protein with the activity of a constitutive triple response (CTR) protein. The invention also provides the coding sequence for the mature mCTR polypeptide, a variant, fragment or modified form thereof, as well as the coding sequence for the mature polypeptide or a fragment thereof in a reading frame with other coding sequences, such as those encoding a leader or secretory sequence, a pre-, pro-, or prepro-protein sequence.

An mCTR polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

In addition to the mCTR nucleic acid and corresponding polypeptide sequences described herein, it is contemplated that variants can be prepared. mCTR variants can be prepared by introducing appropriate nucleotide changes into the mCTR nucleic acid sequence; by synthesis of the desired mCTR polypeptide or by altering the expression level of the mCTR gene in plants. Those skilled in the art will appreciate that amino acid changes may alter post-translational processing of the mCTR polypeptide, such as changing the number or position of glycosylation sites or altering the membrane anchoring characteristics.

In one aspect, preferred mCTR coding sequences include a polynucleotide comprising a nucleic acid sequence which encodes or is complementary to a sequence which encodes a mCTR polypeptide having at least 70%, 75%, 80%, 85%, 90%, 95% or more sequence identity to the amino acid sequence presented in FIG. 2 (SEQ ID NO:2), using a sequence alignment program, as detailed herein.

Sequence variants also include nucleic acid molecules that encode the same polypeptide as encoded by the mCTR polynucleotide sequence described herein. Thus, where the coding frame of an identified nucleic acid molecules is known, for example by homology to known genes or by extension of the sequence, it is appreciated that as a result of the degeneracy of the genetic code, a number of coding sequences can be produced. For example, the triplet CGT encodes the amino acid arginine. Arginine is alternatively encoded by CGA, CGC, CGG, AGA, and AGG. Therefore it is appreciated that such substitutions in the coding region fall within the sequence variants that are covered by the present invention. Any and all of these sequence variants can be utilized in the same way as described herein for the identified mCTR parent sequence.

It is further appreciated that such sequence variants may or may not selectively hybridize to the parent sequence. This would be possible, for example, when the sequence variant includes a different codon for each of the amino acids encoded by the parent nucleotide. Such variants are, nonetheless, specifically contemplated and encompassed by the present invention. In accordance with the present invention, also encompassed are sequences that at least 80% identical to such degeneracy-derived sequence variants.

Although mCTR nucleotide sequence variants are preferably capable of hybridizing to the nucleotide sequences recited herein under conditions of moderately high or high stringency, there are, in some situations, advantages to using variants based on the degeneracy of the code, as described above. For example, codons may be selected to increase the rate at which expression of the peptide occurs in a particular prokaryotic or eukaryotic organism, in accordance with the optimum codon usage dictated by the particular host organism. Alternatively, it may be desirable to produce RNA having longer half lives than the mRNA produced by the recited sequences.

Variations in the native full-length mCTR nucleic acid sequence described herein, may be made, for example, using any of the techniques and guidelines for conservative and non-conservative mutations, as generally known in the art, oligonucleotide-mediated (site-directed) mutagenesis, alanine scanning, and PCR mutagenesis. Site-directed mutagenesis (Kunkel et al., 1991); cassette mutagenesis (Crameri et al., 1995); restriction selection mutagenesis (Haught et al., 1994), or other known techniques can be performed on the cloned DNA to produce nucleic acid sequences encoding mCTR variants.

It is contemplated that the gene sequences associated with the mCTR phenotype may be synthesized, either completely or in part, especially where it is desirable to provide host-preferred sequences. Thus, all or a portion of the desired structural gene (that portion of the gene which encodes the protein) may be synthesized using codons preferred by a selected host. Host-preferred codons may be determined, for example, from the codons used most frequently in the proteins expressed in a desired host species.

It is preferred that an mCTR polynucleotide encodes an mCTR polypeptide that retains triple response activity of the mature mCTR polypeptide encoded by the polynucleotide presented as SEQ ID NO:1.

Variants also include fragments of the mCTR polynucleotide of the invention which can be used to synthesize a full-length mCTR polynucleotide. Preferred embodiments include polynucleotides encoding polypeptide variants wherein 5 to 10, 1 to 5, 1 to 3, 2, 1 or no amino acid residues of a mCTR polypeptide sequence of the invention are substituted, added or deleted, in any combination. Particularly preferred are substitutions, additions, and deletions that are silent such that they do not alter the properties or activities of the polynucleotide or polypeptide.

A nucleotide sequence encoding a mCTR polypeptide can also be used to construct hybridization probes for mapping the gene which encodes a mCTR polypeptide and for further genetic analysis. Screening of a cDNA or genomic library with the selected probe may be conducted using standard procedures, such as described in Sambrook et al., 1989. Hybridization conditions, including moderate stringency and high stringency, are provided in Sambrook et al., supra.

The probes or portions thereof may also be employed in PCR techniques to generate a pool of sequences for identification of closely related mCTR sequences. When mCTR sequences are intended for use as probes, a particular portion of an mCTR encoding sequence, for example a highly conserved portion of the coding sequence may be used.

For example, an mCTR nucleotide sequence may be used as a hybridization probe for a cDNA library to isolate genes, for example, those encoding naturally-occurring variants of mCTR from other plant species, which have a desired level of sequence identity to the mCTR nucleotide sequence disclosed in FIGS. 1A and B (SEQ ID NO:1). Exemplary probes have a length of about 20 to about 50 bases.

As discussed above, nucleic acid sequences of this invention may include genomic, cDNA or mRNA sequence. By "encoding" is meant that the sequence corresponds to a particular amino acid sequence either in a sense or anti-sense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like.

Once the desired form of a mCTR nucleic acid sequence, homologue, variant or fragment thereof, is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

With or without such modification, the desired form of the mCTR nucleic acid sequence, homologue, variant or fragment thereof, may be incorporated into a plant expression vector for transformation of plant cells.

Fragments and variants of the mCTR polypeptide sequence of FIG. 2 (SEQ ID NO:2), are also considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that antigenic or immunogenic in an animal, particularly a human.

mCTR polypeptides of the invention also include polypeptides that vary from the mCTR polypeptide sequence of FIG. 2 (SEQ ID NO:2). These variants may be substitutional, insertional or deletional variants. The variants typically exhibit the same qualitative biological activity as the naturally occurring analogue, although variants can also be selected which have modified characteristics as further described below A "substitution" results from the replacement of one or more nucleotides or amino acids by different nucleotides or amino acids, respectively.

An "insertion" or "addition" is that change in a nucleotide or amino acid sequence which has resulted in the addition of one or more nucleotides or amino acid residues, respectively, as compared to the naturally occurring sequence.

A "deletion" is defined as a change in either nucleotide or amino acid sequence in which one or more nucleotides or amino acid residues, respectively, are absent.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances.

Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids.

Substitutions are generally made in accordance with known "conservative substitutions". A "conservative substitution" refers to the substitution of an amino acid in one class by an amino acid in the same class, where a class is defined by common physicochemical amino acid side chain properties and high substitution frequencies in homologous proteins found in nature (as determined, e.g., by a standard Dayhoff frequency exchange matrix or BLOSUM matrix). (See generally, Doolittle, 1986.)

A "non-conservative substitution" refers to the substitution of an amino acid in one class with an amino acid from another class.

mCTR polypeptide variants typically exhibit the same qualitative biological activity as the naturally-occurring analogue, although variants also are selected to modify the characteristics of the mCTR polypeptide, as needed. For example, glycosylation sites, and more particularly one or more O-linked or N-linked glycosylation sites may be altered or removed. Those skilled in the art will appreciate that amino acid changes may alter post-translational processes of the mCTR polypeptide, such as changing the number or position of glycosylation sites or altering the membrane anchoring characteristics.

The variations can be made using methods known in the art such as oligonucleotide-mediated (site-directed) mutagenesis, alanine scanning, and PCR mutagenesis. Site-directed mutagenesis [Carter et al., 1986; Zoller et al., 1987], cassette mutagenesis [Wells et al., 1985], restriction selection mutagenesis [Wells et al., 1986] or other known techniques can be performed on the cloned DNA to produce the mCTR polypeptide-encoding variant DNA.

Also included within the definition of mCTR polypeptides are other related mCTR polypeptides. Thus, probe or degenerate polymerase chain reaction (PCR) primer sequences may be used to find other related polypeptides. Useful probe or primer sequences may be designed to amplify all or part of the mCTR polypeptide sequence, or sequences outside the coding region. As is generally known in the art, preferred PCR primers are from about 15 to about 35 nucleotides in length, with from about 20 to about 30 being preferred, and may contain inosine as needed. The conditions for the PCR reaction are generally known in the art.

Covalent modifications of mCTR polypeptides are also included within the scope of this invention. For example, the invention provides mCTR polypeptides that are a mature protein and may comprise additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein. [See, e.g., Creighton, T E, 1983].

Proteins can be epitope-tagged by fusing a short antigenic peptide sequence in-frame with the coding sequence of the gene of interest. Epitope tags can be fused to the amino- or carboxy-terminus or internally. An epitope tag allows the detection of the protein fusion with a standard commercial antibody and eliminates the need to generate an antiserum specific to the gene product of interest. In this case, the FLAG® antigenic peptide (DYKDDDDK; Hopp et al., 1988) was fused to the C-terminus of the melon mCTR coding sequence, immediately upstream of the deduced stop codon. Anti-FLAG® monoclonal antibody M2 is used as a primary antibody to immunodetect the tagged protein fusion, and will recognize a FLAG®-tagged fusion protein independent of the intramolecular location of the tag and does not require calcium ions for binding. An anti-FLAG® M2 antibody is commercially available (Stratagene, Sigma or BabCO). FLAG and Anti-FLAG are registered trademarks of Sigma-Aldrich, Inc.

The invention provides a heterologous nucleic acid construct which includes a coding sequence that corresponds to nucleotides 1442 to 3286 of the melon CTR cDNA sequence presented as SEQ ID NO:1). This corresponds to a region that includes the putative kinase domain, but does not include the N-terminal region that has been implicated in binding to the ethylene receptor (Clark et al., 1998).

In one approach to generating mCTR-expressing transgenic plants, a heterologous nucleic acid construct, e.g., a binary Agrobacterium vector construct containing a selectable marker gene was prepared and the mCTR coding sequence expressed under the control of a CsVMV promoter. Plant cells were transformed with the construct and plants regenerated from the transformed plant cells. Example 2 provides the details of a study where Arabidopsis plants were transformed with heterologous nucleic acid constructs comprising the mCTR coding sequence presented as SEQ ID NO:1 or SEQ ID NO:2. The regenerated transgenic plants were observed and/or analyzed and the results showed a modified ethylene response. (See Example 2.)

The present invention also provides a method for interfering with the ethylene response pathway in a plant. The method is carried out by expressing the nucleic acid sequence which encodes mCTR, or a fragment that includes the kinase domain, resulting in negative regulation of the ethylene response or perception pathway in the plant. In a related aspect, the invention provides a method for producing a plant with a modified ethylene response, wherein the plant expresses mCTR or a biologically active fragment thereof, e.g., the kinase domain.

B. Vectors for Expression of mCTR Nucleic Acids in Plants

The present invention provides vectors suitable for the transformation of plants. The vectors, chimeric genes and DNA constructs of the present invention are useful for the expression of the full-length melon mCTR coding sequence or fragments thereof. Transgenic plants, transgenic plant cells and transgenic fruit, carrying the chimeric genes of the present invention, exhibit a modified ethylene response.

The construction of vectors for use in practicing the present invention are generally known to those of skill in the art. (See generally, Mandates, et al., Molecular Cloning: A LABORATORY MANUAL, 2d Edition (1989), and Ausubel, F E M., et al., Eds., CURRENT PROTOCOLS IN MOLECULAR BIOLOGY, John Wiley & Sons, Inc., Copyright (c)1987, 1988, 1989, 1990, 1993 by Current Protocols; Elvin, S. B., Schilperoort, R. A., Varma, D. P. S., eds. Plant Molecular Biology Manual (1990), all three of which are expressly incorporated by reference, herein.

Binary Ti-based vector systems include plasmids containing at least one T-DNA border sequence (left, right or both), restriction endonuclease sites for the addition of one or more heterologous nucleic acid sequences [adjacent flanking T-DNA border sequence(s)], a heterologous nucleic acid sequence (i.e., the mCTR coding sequence or a fragment thereof), operably linked to appropriate regulatory sequences and to the directional T-DNA border sequences, a selectable marker which is functional in plant cells, a heterologous Ti-plasmid promoter, and an E. coli origin of replication.

In one general application of the method, an Agrobacterium binary plant transformation vector is introduced into a disarmed strain of A. tumefaciens by electroporation (Nagel et al., 1990), followed by co-cultivation with plant cells, resulting in transfer of the heterologous nucleic acid sequence into plant cells. In general, co-cultivation is carried out for two or three days in the absence of feeder cells or a nurse culture.

Standard Agrobacterium binary vectors are known to those of skill in the art and many are commercially available, an example of which is pBI121 (Clontech Laboratories, Palo Alto, Calif.), as further described, above. Preparation of *Agrobacterium tumefaciens* cultures is carried out using methods generally known in the art.

Such expression vectors may have single or multiple transcription termination signals at the 3' end of the DNA sequence being expressed. The expression cassette may also include, for example, (i) a DNA sequence encoding a leader peptide (e.g., to allow secretion or vacuolar targeting), (ii) translation termination signals, (iii) a selectable marker gene for use in plant cells, (iv) sequences that allow for selection and propagation in a secondary host, such as an origin of replication and a selectable marker sequence.

Expression of a selectable marker gene permits selection of transformed plant cells containing the gene by rendering the cells resistant to an amount of an antibiotic that would be toxic to non-transformed plant cells. Exemplary selectable marker genes for use in practicing the present invention include the neomycin phosphotransferase (nptII) resistance gene, hygromycin phosphotransferase (hpt), bromoxynil-specific nitrilase (bxn), phosphinothricin acetyltransferase enzyme (BAR) and the spectinomycin resistance gene (spt), wherein the selective agent is kanamycin, hygromycin, geneticin, the herbicide glufosinate-ammonium ("Basta") or spectinomycin, respectively.

Typical secondary hosts include bacteria and yeast. In one embodiment, the secondary host is *Escherichia coli*, the origin of replication is a colE1-type, and the selectable marker is a gene encoding ampicillin resistance. Origin of replication and selectable marker sequences operative in secondary hosts are well known in the art and many are commercially available (e.g., Clontech, Palo Alto, Calif.; Stratagene, La Jolla, Calif.).

In another embodiment, the methods of the invention are carried out using a vector carrying the kanamycin resistance gene.

In yet another embodiment, the methods of the invention are carried out using a vector that includes the bar gene from Streptomyces, which encodes phosphinothricin acetyl transferase (PAT), that inactivates the active ingredient in the herbicide bialaphos, phosphinothricin (PPT). PPT inhibits glutamine synthetase, causing rapid accumulation of ammonia and cell death. Transgenic plants containing this gene exhibit tolerance to the herbicide, "BASTA". This gene can also be used as a selectable marker gene, since explants carrying the bar gene are capable of growing on selective media containing phosphinothricin (PPT), which is an active component of bialaphos.

In further embodiments, the methods of the invention are carried out using a vector which includes an herbicide resistance gene, conferring resistance to glyphosate-containing herbicides. Glyphosate refers to N-phosphonomethyl glycine, in either its acidic or anionic forms. Herbicides containing this active ingredient include "ROUNDUP" and "GLEAN". Exemplary genes for imparting glyphosate resistance include an EPSP synthase gene (5-enolpyruvyl-3-phosphosshikimate synthase) or an acetolactate synthase gene.

The particular marker gene employed is one which allows for selection of transformed cells as compared to cells lacking the DNA which has been introduced. Preferably, the selectable marker gene is one which facilitates selection at the tissue culture stage of the functional gene discovery system, e.g., a kanamyacin, hygromycin or ampicillin resistance gene.

The selection of an appropriate promoter effective to express the selectable marker-encoding sequence and the termination element for the selectable marker-encoding sequence may be accomplished by the use of well known, and/or commercially available sequences.

One exemplary binary vector construct for over-expression of the melon mCTR homologue in transgenic plants includes the melon mCTR cDNA fused to a constitutive promoter from cassava vein mosaic virus (Verdaguer et al., 1996), a nos 3' termination sequence from *Agrobacterium tumefaciens* (Depicker et al., 1982), a selection cassette composed of the nptII gene conferring kanamycin resistance under the transcriptional control of a constitutive promoter (e.g., the raspberry E4 promoter "RE4"; U.S. Pat. Nos. 5,783,393; and 5,783,394) and the *Agrobacterium tumefaciens* gene 7 termination sequence within the T-DNA borders (Beck et al., 1982; Velten et al., 1985). Exemplary vectors include the pGPTV binary vector (Becker et al., 1992) and the pPZP200 binary vector (Hajdukiewicz et al., 1994).

Exemplary promoters effective to express mCTR or a fragment thereof include constitutive, inducible, tissue-associated and/or an ethylene responsive promoters. Constitutive promoters such as the raspberry E4 promoter (RE4, U.S. Pat. Nos. 5,783,393; and 5,783,394), the 35S CaMV promoter or the CsVMV promoter (Cassava Vein Mosaic Virus promoter, Verdaguer et al., 1998); fruit-associated promoters selected from the group consisting of a cherry 29 (CH29) promoter (Fils-Lycaon et al., 1996), an mf60 promoter (Yamada et al., 1999); a Thi::actin, aThi 1.3::intron (described in co-owned 09/560,419, expressly incorporated by reference herein), a dru 1.3 promoter (described in co-owned U.S. Pat. No. 5,783,394, expressly incorporated by reference herein), a MADS2 promoter, a fuji Thi 1.3 and a Thi 1.0 fruit-associated promoter (described in co-owned U.S. S No. 60/132,124, expressly incorporated by reference herein); melon fruit-associated promoters (described in U.S. S No. 60/190,414, expressly incorporated by reference herein) including a cmACO1/TE4 promoter, a MEL7 promoter, a MEL2 promoter, a 6E promoter and a 2F promoter; and ethylene inducible promoters such as an E8 promoter, an E4 promoter (Deikman, et al., 1992; Xu et al. 1996; Deikman et al., 1988) and an E8::E4 promoter may be used (described in co-owned U.S. Ser. No. 09/157,077, expressly incorporated by reference herein; Clendennen et al., 1999); a banana TRX promoter, TRX fusion promoter and a banana PEL promoter (described in co-owned U.S. Ser. No. 09/527,972, expressly incorporated by reference herein).

Further, the invention includes a method for producing a transgenic plant, where fruit, vegetable or flowers produced by the plant have a modified ethylene response phenotype. In this method a heterologous gene construct is introduced (e.g., by transformation) into progenitor cells of the plant. An exemplary heterologous gene construct is composed of (i) a DNA sequence encoding mCTR or a fragment thereof, operably linked to: (ii) a promoter effective to express the mCTR coding sequence or fragment thereof in plant cells. The mCTR DNA sequence is heterologous to the promoter and the chimeric gene contains the appropriate regulatory elements necessary for expression in a plant cell. Transformed progenitors are grown to produce a transgenic plant. The method further includes transforming plant cells with a vector containing a selectable marker and an mCTR coding sequence. (See Example 2.)

C. Transformation of Plant Cells

The invention provides, plants derived from cells transformed with a vector comprising an mCTR coding sequence. Such transformed plants have a modulated response to ethylene. In a preferred embodiment, the expression of a modified mCTR nucleic acid confers a phenotype on the plant characterized by a decrease in the response to ethylene as compared to a corresponding non-transformed plant. Thus, for example, when the modified mCTR nucleic acid is expressed in fruit such as tomato, the fruit ripening process is retarded thereby reducing spoilage and extending the shelf life and/or harvesting season for the fruit. The invention finds further utility in preventing spoilage of vegetative tissue and in enhancing the longevity of cut flowers.

A chimeric gene (heterologous nucleic acid construct) containing an mCTR coding sequence may be transferred into plant cells by any of a number of plant transformation methodologies, including Agrobacterium-based methods [Ranier et al., 1990 (rice); McCormick et al., 1986 (tomato); Norelli et al., 1996 (apple)], electroporation, microinjection, and microprojectile bombardment. (See, e.g., Comai et al., 1993; Klein et al., 1988; Miki et al. 1987; Bellini et al., 1989).

In one approach, the heterologous nucleic acid construct is introduced into a plant by way of a T-DNA-less Ti plasmid carried by *Agrobacterium tumefaciens,* followed by co-cultivation of *A. tumefaciens* with the plant cells. In such cases, vectors for use in the invention contain a selectable marker gene, T-DNA border regions from *Agrobacterium tumefaciens,* an mCTR coding sequence and additional elements necessary for expression in plant cells. Exemplary Agrobacterium transformation vectors are commercially available, e.g., from Clontech (Palo Alto, Calif.) and further described by An et al., 1985.

Other suitable vectors may be constructed using a selected promoter together an mCTR coding sequence, a selectable marker encoding nucleic acid sequence under the control of a promoter and additional elements necessary for expression in plant cells in a standard plant transformation vector, many of which are available both commercially (e.g., Clontech, Palo Alto, Calif.) and from academic sources [e.g., Salk Institute, Plant Biology Labs; Texas A & M University; Waksman Institute, Rutgers; The State University of New Jersey, Piscataway, N.J.].

In another approach, the heterologous nucleic acid construct is introduced into plant cells by way of microprojectile bombardment using microparticles loaded with DNA which are bombarded into the cells using "gene gun" technology. (See, e.g., Robinson et al., 1997.) When electroporation or microprojectile bombardment transformation techniques are utilized, the transformation vector generally comprises the mCTR coding sequence and a selectable marker coding sequence and associated promoter together with additional elements necessary for expression in plant cells.

Transformed plant cells are obtained as a result of introduction of such a heterologous nucleic acid construct into plant progenitor or explant cells. The plant cells are cultured in medium containing the appropriate selection agent to select for and identify plant cells which are transformed. After transformed plant cells are selected, whole plants are regenerated from the transgenic plant cells. Techniques for regenerating whole plants from transformed plant cells are generally known in the art.

Preferred plants suitable for transformation using the heterologous nucleic acid constructs described herein and for expression of an mCTR coding sequence include, but are not limited to, apple; tomato; pineapple; grape; raspberry; strawberry; kiwi fruit; avocado; melon; mango; papaya; peach; pear; cherry; citrus; date palm; plantain; soybean; cotton; alfalfa; oilseed rape; flax; sugar beet; sunflower; potato; tobacco; maize; wheat; rice; nuts; vegetables including broccoli, cauliflower, squash and lettuce; and flowers, including cut flowers such as carnation, iris, rose, daisy, lily, snapdragon and petunia, etc.

Particularly preferred plants for the expression of mCTR or the kinase domain thereof include, but are not limited to, tomato, lettuce, melon and other crops where a reduction in the ethylene response and a corresponding reduction or elimination in the a undesirable physiological effects of post harvest ethylene exposure are desirable.

In one exemplary embodiment, cotyledon explants of a commercial cantaloupe variety (*Cucumis Melo,* Muskmelon) are transformed according to known methods (Fang et al., 1990; Valles et al., 1994; Dong et al., 1991; Gonsalves et al., 1994; Yoshioka et al., 1992; Ayub et al., 1996), using a disarmed Agrobacterium strain to introduce a binary vector into plants. The disarmed Agrobacterium strain is co-cultivated with melon cotyledon tissue explants, and primary transformants are selected on the basis of their capacity to regenerate and develop roots on media containing the antibiotic, kanamycin.

In other exemplary embodiments, Agrobacterium transformation methods as previously described for banana, rice, tomato and apple are used to transform plant cells using a promoter selected from those described above. [See, e.g., Sagi et al., 1995 (banana); Ranier et al., 1990 (rice); McCormick et al., 1986 (tomato); and Norelli et al., 1996 (apple).]

In one aspect, a heterologous nucleic acid construct containing an mCTR coding sequence is used to develop transgenic plants which exhibit a modulated ethylene response resulting in an altered ripening phenotype and delayed senescence of transgenic fruit, vegetables or flowers produced by the plants.

A modified ethylene response phenotype refers to an alteration in the rate of ripening; characterized by an increased ripening time course or prolonged ripening and delayed senescence as observed for fruit or vegetables derived from an mCTR-expressing transgenic plant relative to fruit or vegetables derived from a corresponding non-transgenic plant. In cut flowers, a modified ethylene response phenotype is evidenced by delayed leaf and petal abscission and browning, together with reduced or delayed stem wilting.

IV. Evaluation of Transformants

In accordance with the claimed invention, a plant which has a decreased response to ethylene ("an ethylene insensitive plant") may be analyzed using a number of approaches. In one approach, the plant is evaluated for a typical ethylene response when treated with a high concentration of ethylene.

As defined herein, an ethylene insensitive plant is a transgenic plant that displays a response to ethylene which is decreased relative to the same type of plant of a similar age and grown under similar conditions that has not been transformed with a heterologous nucleic acid construct comprising an mCTR coding sequence. Transgenic plants may also be evaluated by DNA PCR and/or Southern blot to determine if the mCTR transgene has been incorporated in the plant genome; for the expression of the transgene by Northern Blot and/or RT-PCR; and for mCTR protein expression by immunoassay or Western blot.

A. Evaluation of Ethylene Reponses

A typical ethylene response in wild type plants includes, for example, the so-called "triple response" which involves inhibition of root and stem elongation, radial swelling of the stem, and absence of normal geotropic response, e.g. diageotropism (defined as "upward" elongation of the hypocotyl/stem and "downward" elongation of roots). Thus, for example, ethylene insensitive plants may be created in accordance with the present invention and identified as having an altered "triple response" to ethylene, wherein the root and stem are elongated despite the presence of high concentrations of ethylene. The seedling ethylene triple response is characterized by a short root, a short, thick hypocotyl and a pronounced apical hook and may be quantitated by measurement of hypocotyl length.

Further, a typical ethylene response includes a shut down or diminution of endogenous ethylene production, upon application of high concentrations of ethylene. Hence, transgenic plants may also be screened for continued ethylene production, despite administration of high concentrations of ethylene, as an indicator of ethylene insensitivity. Such screening may include screening for root or stem elongation and screening for increased ethylene production.

Ethylene sensitive wild type plants experience an inhibition of root and stem elongation when an inhibitory amount of ethylene is administered. An inhibition of root and stem elongation means that the roots and stems grow less than they typically would without application of an inhibitory amount of ethylene. Ethylene sensitive wild type plants experience a shut down or diminution of endogenous ethylene production, upon application of high concentrations of ethylene. In ethylene insensitive plants such a shut down or diminution of endogenous ethylene production is not observed in response to administration of inhibitory amounts of ethylene. Generally, in carrying out ethylene sensitivity assays, wild type and transgenic plants are compared to one another. As will be understood by those of skill in the art, the absolute level of ethylene production will vary based on the type of plant, the growth conditions, etc.

B. DNA PCR and Southern Blot

Transformation of each plant may be confirmed by carrying out a Southern blot analysis of genomic DNA. Typically, total DNA is isolated from each transformant (e.g., Schwarz-Sommer et al., 1992). The DNA is then digested with restriction enzyme, fractionated in an agarose gel and transferred to nitrocellulose filters (e.g., HYBOND-N, Amersham) or nylon membranes, according to standard techniques. The blot is then probed, e.g., with $^{32}$P-labeled mCTR cDNA. Procedures for restriction digestion, gel electrophoresis, Southern transfer and hybridization are as described by Maniatis et al., 1989, expressly incorporated by reference herein.

Transformation of each plant may also be confirmed by polymerase chain reaction (PCR) in a reaction mixture including the components necessary for amplification of specific nucleic acid sequences. Kits and reagents for carrying out PCR are commercially available, for example, a Taqman™ probe and primer set available from Perkin Elmer Applied Biosystems.

In one approach, DNA is extracted from various tissues of transgenic plants and analyzed for the presence of an mCTR coding sequence by polymerase chain reaction (PCR), using procedures routinely employed by those of skill in the art. PCR is carried out using oligonucleotide primers specific to an mCTR coding sequence. Example 2 describes the DNA PCR analysis of Arabidopsis lines transformed with heterologous nucleic acid constructs comprising mCTR coding sequences. (See also FIG. 4.)

C. Northern Blot

RNA may be isolated from specific plant tissues and separated, e.g., in a 1.2% agarose gel containing 2.2M formaldehyde, then blotted to a nylon filter, e.g., Hybond-N, according to the standard procedures routinely used in the art. Strand specific RNA probes may be synthesized by phage T7 and T3 RNA polymerases from a cDNA clone for mCTR. This allows for a determination of the presence and an estimation of the amount of mRNA resulting from expression of mCTR in various tissue of the plant. Northern analysis may be carried out as described in Maniatis et al., 1989.

D. RT-PCR

RNA may also be extracted from various plant tissues, followed by reverse transcription of mRNA and amplification of partial cDNA sequences by reverse transcriptase-polymerase chain reaction (RT-PCR), using methods generally known in the art and reagents which commercially available (e.g., from Perkin Elmer Applied Biosystems).

Example 2 describes the RT-PCR analysis of Arabidopsis lines transformed with heterologous nucleic acid constructs comprising mCTR coding sequences. (See also FIG. 5.)

E. Immunoassay or Western blot

An ELISA, Western blot or immunodotblot immunoassay may also be conducted on putative transformants to detect the presence of an mCTR protein, as generally described in Harlow et al., 1988. Standard techniques for western blotting are known in the art, e.g., the protocol described in Glick et al., 1993.

Given an antibody that is specifically immunoreactive with a mCTR protein or polypeptide, any of a number of different types of immunoassays may be employed by one of skill in the art to detect the presence of a mCTR protein in tissues of transgenic plants.

V. Utility

Interfering with the ethylene perception pathway is an alternative approach to the downregulation of ethylene biosynthesis as a means to regulate the effect of ethylene in plants. In carrying out this approach, ethylene-mediated responses such as fruit ripening, vegetable ripening, flower senescence, abscission, and other undesirable ethylene responses are blocked or delayed. The present invention is directed to mCTR nucleic acids, mCTR proteins and the expression of mCTR protein coding sequences in plants. Transgenic plants which express mCTR and exhibit a modulated triple response find utility in the inhibition or elimination of the deleterious effects of ethylene on fruits, vegetables and flowers.

In general, the utility of creating a low ethylene phenotype by interfering in ethylene perception has been proven by the success of chemicals such as Methylcyclopropene (MCP). The genetic interference in ethylene perception in transgenic plants that express mCTR may be used alone or together with expression of a gene product capable of reducing ethylene biosynthesis when expressed in plant cells, e.g., S-adenosyl-methionine hydrolase (SAMase), thereby reducing the effects of ethylene on post harvest physiology of fruits, vegetables and flowers.

The following example illustrates but is not intended in any way to limit the invention.

EXAMPLE 1

Oligonucleotide primers complementary to conserved domains of the CTR1 cDNA sequences from Arabidopsis and tomato were used to amplify a full-length cDNA encoding a homologue of CTR1 from a cantaloupe (*Cucumis melo*) fruit cDNA library.

Degenerate oligonucleotide primers were designed to amplify the 5' and 3' ends of a CTR1 homologue from a PCR-accessible cDNA library from ripe melon fruit. Putatively conserved regions of CTR1 were selected by aligning the nucleotide sequence of GenBank Accession Nos. L08789 (*Arabidopsis thaliana* CTR1 cDNA) and Y13272 (tomato CTR1-like cDNA). A reverse primer CTR1 2-R (SEQ ID NO:3) was designed to perform a 5' RACE to amplify the response regulator region of a melon CTR1 homologue, resulting in a 1.3 kb fragment, while CTR1 3-F (SEQ ID NO:4) was designed for 3' RACE to isolate the kinase domain, resulting in the isolation of a 1.4 kb fragment. The two conserved domains are separated by a highly variable region, and so specific primers were designed from the melon RACE products to amplify this variable region from melon. The two primers, mCTR5-F (SEQ ID NO:5) and mCTR6-R (SEQ ID NO:6), were used in an RT-PCR reaction to amplify a 500 bp fragment that overlaps the 5' and 3' fragments previously obtained by RACE. Finally, the 3.2 kb complete mCTR cDNA (SEQ ID NO:1) was assembled from the three fragments by PCR without the addition of oligonucleotide primers. The full-length mCTR coding region was epitope-tagged at the C-terminus in order to monitor protein expression in transformed plants.

A Basic BLASTN search of non-redundant nucleic acid sequences, conducted on May 25, 2000, through NCBI using the search capabilities of the NIH website with the nucleotide sequence presented in FIGS. 1A–1B (melon mCTR homologue nucleic acid sequence). A Basic BLASTP search of non-redundant SwissProt sequences, was also conducted on May 25, 2000, through NCBI using the search capabilities of the NIH website with the amino acid sequence presented in FIG. 2. When compared to Arabidopsis CTR1, the melon mCTR sequence is 58% identical at the nucleotide level and 62% identical at the amino acid level. When compared to tomato CTR1, the melon mCTR sequence is 57% identical at the nucleotide level and 58% identical at the amino acid level. In addition, the melon sequence shows significant conservation in the putative kinase encoding region, suggesting that the cDNA is likely to encode a protein with kinase activity in melon.

EXAMPLE 2

A prokaryotic mCTR expression cassette was epitope-tagged and verified by expression and detection in *E coli* before being used to generate plant expression constructs. Binary constructs were made that place the mCTR gene under the control of the CsVMV constitutive promoter and further contain the nptII gene for conferring kanamycin resistance. Construct pAG4224 contains the full-length melon CTR coding region which has the sequence presented as SEQ ID NO: 1, while construct pAG 4225 contains the kinase domain alone, which has the sequence presented as nucleotides A-3286 of SEQ ID NO:1, wherein A is any one of nucleotides 1440–1444.

Arabidopsis (Col-0) was individually transformed with pAG4224 and pAG4225, described above. Transformed plants (T1) were selected on kanamycin and transferred to soil. The T1 plants were allowed to self and T2 seed was collected from each event. T2 seed from six independently transformed lines expressing the mCTR full-length cDNA (4224) and five lines expressing mCTR kinase only (4225) were plated on solid media supplemented with 100 µM ACC, which is constitutively converted to ethylene in the seedlings.

An assay for the ethylene triple response was conducted using Arabidopsis seedlings germinated on solid nutrient medium or on the same medium supplemented with 100 µM ACC. Hypocotyl length was used as a measure of the ethylene triple response. Untransformed Arabidopsis (Col0), the ethylene insensitive mutant ein2-1 and the constitutive ethylene response mutant ctr1 were included as controls for the treatment. The seeds were stratified 4° C. (3 days), then transferred to 25° C. light (9 hours) and then 25° C. dark (3 days). Seedlings were observed and the hypocotyl length of at least 20 seedlings per line was measured to the nearest mm. The mean hypocotyl length (+SD) of untransformed Arabidopsis (Col-0), the two ethylene response mutants, and 5 independent transformation events for each mCTR expression construct is provided in FIG. 3. The results show that the ethylene response mutants ctr1 and ein2-1 each exhibited the predicted phenotype on ACC, while most of the transformed Arabidopsis lines showed an attenuated ethylene response in the presence of ACC (a longer hypocotyl and less pronounced apical hook). In particular, events 4225P, 4225X, 4225R and 4224AB had mean hypocotyl lengths significantly different from the untransformed control (Col-0). The increase in mean hypocotyl length in most of the transformed of the lines supports the observation that the mCTR transformants are partially insensitive to ethylene. (See FIG. 3.)

Molecular analysis was performed on the lines showing the most extreme ethylene resistance based on hypocotyl measurements. The analysis confirmed the presence of both the mCTR transgene and the transcript associated with it consistent with the observations of a modified triple response (FIG. 3). DNA PCR using genomic DNA as the template to confirm the presence of the transgene was performed on kanamycin resistant seedlings using the Extract-N-Amp Plant PCR Kit according to the manufacturer's protocol (Sigma, cat# XNA-P).

The template for the PCR reactions was either a single seedling that was kanamycin-resistant (4224AB through 4225X) or a leaf sample collected from each of five individual seedlings transplanted to soil after the kanamycin selection (individuals 1–5 from event 4225P).

Figure 4:
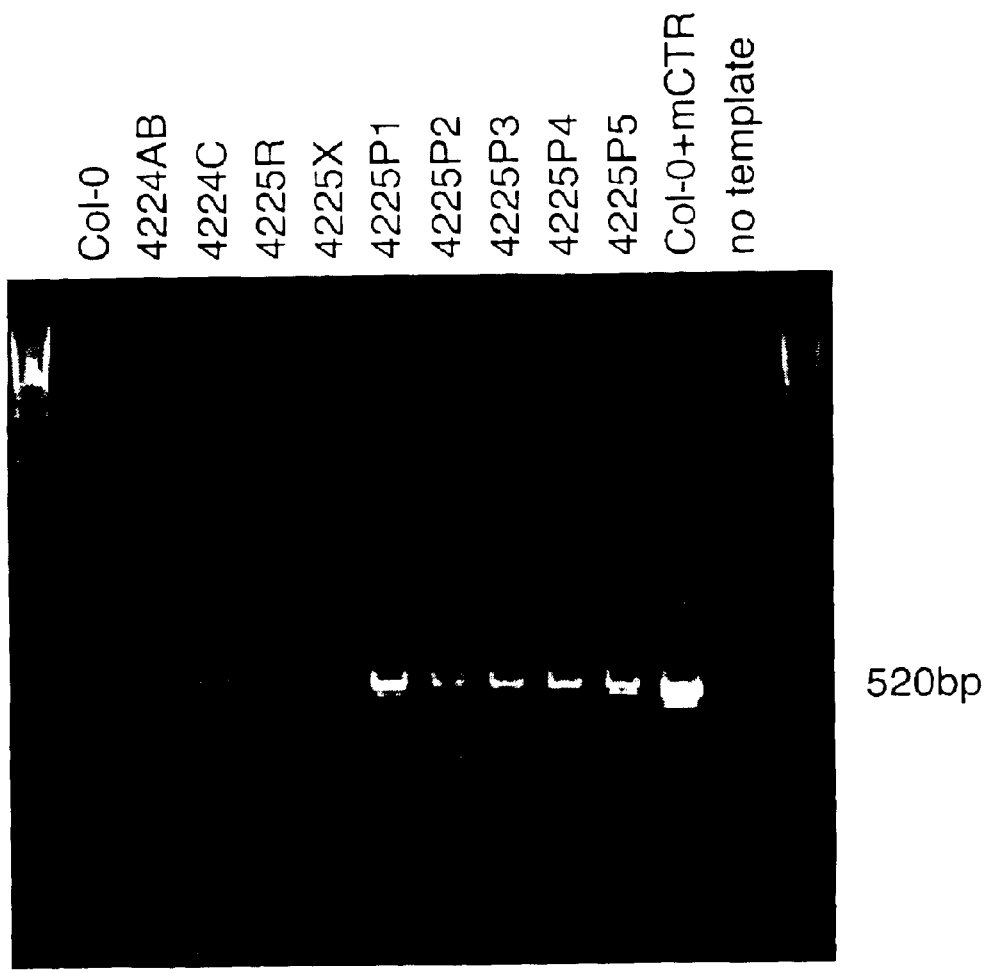
FIG. 4 is an image of an ethidium bromide stained gel showing the results of electrophoresis of DNA PCR products derived by amplification of genomic DNA taken from untransformed Arabidopsis seedlings (Col-0) or seedlings from Arabidopsis lines transformed with the pAG4224 (4224AB, 4224C) and pAG4225 (4225X, 4225P1, 4225P2, 4225P3, 4225P4 and 4225P5) construct.

The results shown in FIG. 4 confirm the presence of the mCTR transgene in kanamycin resistant seedlings. The expected 520 bp product was obtained following DNA PCR of transgenic lines, but was observed to be absent in untransformed Col-0 DNA and in the absence of template. A positive control for the reaction consisted of Col-0 DNA supplemented with the mCTR expression construct pAG4225 (FIG. 4).

Figure 5:
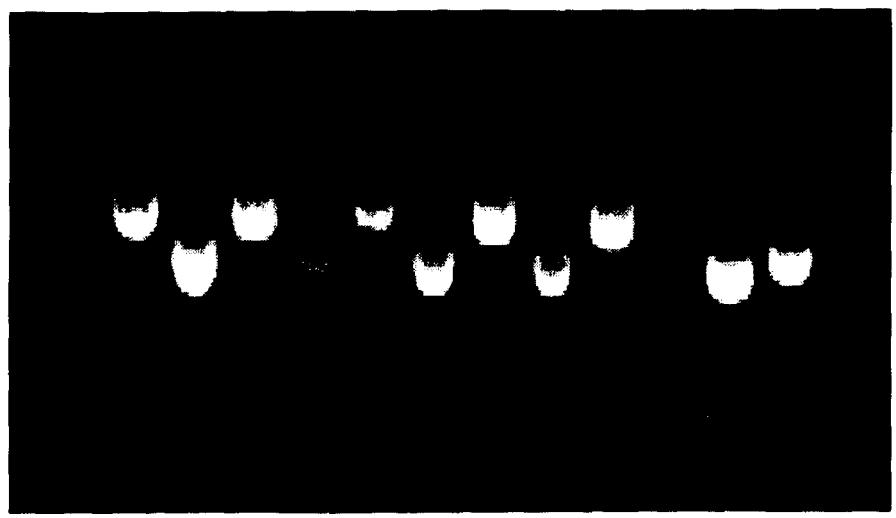
FIG. 5 is an image of an ethidium bromide stained gel showing the results of electrophoresis of RT-PCR products derived by amplification of RNA taken from seedlings from Arabidopsis lines transformed with the pAG4224 (4224AB) or pAG 4225 (4225P, 4225R, 4225P2, 4225X) construct and untransformed Arabidopsis seedlings (COL-0), with primers specific for actin (A) or melon CTR (C).

RNA was extracted directly from a pool of seedlings taken directly from the ACC plates where the ethylene-resistant phenotype was confirmed using a modified CTAB extraction protocol. RT-PCR was performed using a TITANIUM One-Step RT-PCR Kit (Clontech, cat# K1403–2) according to the supplier's protocol. In both reactions, the primers used were specific the melon CTR sequence upstream of the kinase domain, a region which occurs in both mCTR expression constructs, mCTR8-F (SEQ ID NO:8) and mCTR9-R (SEQ ID NO:8). Results of the RT-PCR indicate that a 520 bp product is amplified from the transgenic lines, but not from the untransformed Col-0, with an actin-specific transcript used as a positive control for each sample (FIG. 5).

TABLE 1

Sequences Provided in Support of the Invention

| Description | SEQ ID NO |
|---|---|
| the 3286 nucleotide sequence of the *Cucumis melo* CTR1 homologue, as shown in FIGS. 1A–B | 1 |
| the deduced 850 amino acid sequence of the *Cucumis melo* CTR1 homologue, as shown in FIG. 2 | 2 |
| CTR1 2-R: (5') CAA TAT TTA CAT CCY TTG GCA ATT CGA C (3'), where y is T or C, s is G or C, and k is G or T. | 3 |
| CTR1 3-F: (5') CGT GST GAK TGG CAT GGC TCK GAT GTT GC (3'), where y is T or C, s is G or C, and k is G or T. | 4 |
| mCTR 5-F: (5') ATG TTT GGG ATC TGC TGT GAT TCC (3') | 5 |
| mCTR 6-R: (5') TTT GGT GGC TTG GTC ACC GCA CCC (3') | 6 |
| mCTR 8-F: (5') CATGTGTTGCTTCTCCATATAGTG (3') | 7 |
| mCTR 9-R: (5') TCATCTATGTCTTTGACACCTGAC (3') | 8 |

All publications, patents and patent applications are herein expressly incorporated by reference in their entirety to the same extent as if each individual publication, patent or patent application was specifically and individually indicated to be incorporated by reference in its entirety.

---

What is claimed is:

1. An isolated nucleic acid encoding a protein with the activity of a constitutive triple response (CTR) protein, said nucleic acid comprising the nucleotide sequence of SEQ ID NO: 1.

2. An isolated nucleic acid that specifically hybridizes under highly stringent conditions to the complement of the sequence set forth in SEQ ID NO: 1, wherein the nucleic acid encodes a protein with the activity of a constitutive triple response (CTR) protein.

3. An isolated nucleic acid comprising a nucleotide sequence that encodes the amino acid sequence of SEQ ID NO: 2.

4. An isolated nucleic acid encoding a protein with the activity of a constitutive triple response (CTR) protein, said nucleic acid comprising nucleotides 1444–3286 of SEQ ID NO: 1.

5. An isolated nucleic acid that specifically hybridizes under highly stringent conditions to the complement of nucleotides 1444–3286 of SEQ ID NO: 1, wherein the nucleic acid encodes a protein with the activity of a constitutive triple response (CTR) protein.

6. An isolated vector comprising the nucleic acid of any one of claims 1, 2, 3, 4, or 5.

7. The isolated vector of claim 6, wherein said nucleic acid is operably linked to a transcription regulatory element.

8. An isolated host cell comprising the isolated nucleic acid of any one of claim 1, 2, 3, 4, or 5.

9. An isolated host cell comprising the vector of claim 6.

10. A transgenic cell comprising the vector of claim 6.

11. transgenic cell comprising the nucleic acid of any one of claims 1, 2, 3, 4, or 5.

12. A mature transgenic plant comprising the cell of claim 10.

* * * * *

SEQUENCE LISTING

<160> NUMBER OF SEQ ID NOS: 8

<210> SEQ ID NO 1
<211> LENGTH: 3286
<212> TYPE: DNA
<213> ORGANISM: Cucumis melo
<220> FEATURE:
<221> NAME/KEY: misc_feature
<222> LOCATION: (81)...(81)
<223> OTHER INFORMATION: n = A,T,C or G
<221> NAME/KEY: misc_feature
<222> LOCATION: (593)...(594)
<223> OTHER INFORMATION: n = A,T,C or G

<400> SEQUENCE: 1

```
attcgattgt cgggaagaga gagcagaaaa ttaaaaccag aatctccaac acacaaacct     60
tccacccctt caacaatggc nggattctag ggtttctatg ggtttaaggt gatacagttt    120
cctaatttct ccatggaaat gcctggacgg aggtctgatt actctctttt aagtcaaatt    180
ccggacgagg aggttggaac gggagcttcc acttcctttt acgactccgt agcagctggg    240
ggaaacgtta tcaaagggag aaccgatagg gttttgatt gggatgggag tggtgatcac    300
aggttaaaca cgcaggcgta tcggataggg aacctgtatt catggattgg tttacagaga    360
cattccagtg gaagcagcta cgatgatagc tctctctcta gtgattacta cgcaccgacg    420
ctatcaaacc ctgcagcaaa tgagatcaat gcattggaat atatcctcga tgatgatttc    480
cgagtgatga agctgtggg aagtggaggt tcgtctggaa agagctgggc ccagcagacg    540
gaagagagct ttcagttgca gcagcccttg gttcttaggc tttcttcaga tgnnacttgt    600
gccgatgatc ccaactttat ggatccgatt ccagacgagg cagctttaag atcgttatcg    660
atttcagctg aggccatctc gcatcggttc tgggtaaatg gatgcatgtc atatttggag    720
```

-continued

| | |
|---|---|
| aaagtgccag atggtttta tctaattcat gggatggacc catatgtatg gtcattatgc | 780 |
| accaatctgc aagaggatgg gcgtatacca tcatttgaat ctctgaaaac agttgattcc | 840 |
| agcatcggtt catcaattga agtagttttg atagatcggc atagtgatgc tagcttaaaa | 900 |
| gaactgcaaa acagggtgca taatatttct tccagttgtg taaccacaaa agaggttgca | 960 |
| gatcatatag caaagctggt atgcaatcac ttgggggtt cagtttctga gggagaagat | 1020 |
| gacttggttt ctgcctggaa ggaatgcagc gatgacttaa aggaatgttt gggatctgct | 1080 |
| gtgattccct tatgcagctt atctgttggc ctttgtagac atcgtgctct tttattcaaa | 1140 |
| gtcctagctg attcaattga tttaccctgt cgaattgcca aaggatgtaa atattgcact | 1200 |
| agagatgatg cttcatcttg ccttgttagg ttcgggcttg atagggaata tctcatcgat | 1260 |
| ctgattggga ggccaggttg cttatgccaa cctgattctt tgctcaatgg tccatcatcc | 1320 |
| atctcaattt cttcaccatt gcgatttcca agactaaaac ctattgaatc taccattgat | 1380 |
| ttcaggtcac tggccaaaca gtatttcttg gatagccaat cacttaatct tgtatttgat | 1440 |
| gaagcttctt caggtaatgt tgtatctggg aaggatgctg cattctccgt ctatcaaagg | 1500 |
| ccattaaata ggaaggatgt agatggaaaa accatagtgg ttactggtga caaggacaga | 1560 |
| aattctcagt tattaaataa aaaagcagcc caactgaata ctcaagatgg aaagtctgag | 1620 |
| caatttagat catgtgttgc ttctccatat agtgtacagt cgacccctt tgtagaaaat | 1680 |
| gtagtccctt taagccatat ctcacacatt ggttctgaag attcggagca tctcttagca | 1740 |
| ttgtctcatc caaggatgga tcatgttaac aatttaccat ttgttcatgg tagtcagttg | 1800 |
| attagaaaac caaatgagct ttcccttggc ttagaagatt tggttattcc atggacagat | 1860 |
| cttgatttga gggagaaaat tggagcaggt tcttttggga ctgtatatcg tggtgagtgg | 1920 |
| catggctctg atgttgctgt gaagatcctc acagaacaag acttccatcc tgaacgtgtt | 1980 |
| aatgagtttc tgagagaggt tgctatcatg aaatctttac gacatcctaa tattgtactg | 2040 |
| tttatgggtg cggtgaccaa gccaccaaac ttgtccattg tcaccgaata tctatcgaga | 2100 |
| ggtagcttgt ataggctttt gcataagtca ggtgtcaaag acatagatga aacacgtcga | 2160 |
| ataaatatgg cttttgatgt ggcaaaggga atgaactacc tccacagacg tgatcctcca | 2220 |
| attgttcatc gtgatttaaa atcaccgaat ctgttagttg acaagaagta tacagtcaag | 2280 |
| gtttgtgatt tggtctctc ccgtttaaag gcacgcacat ttctttcatc caaatctgca | 2340 |
| gctggaacac ctgaatggat ggcaccagaa gtactacgcg atgaaccatc aaatgaaaag | 2400 |
| tcagatgttt acagctttgg agtgattttg tgggagttgg caactttgca acagccatgg | 2460 |
| tgtaatctaa acccagctca ggttgtcgca gctgttggat ttaagggcaa aaggcttgac | 2520 |
| atcccacgtg atgtaaatcc caaattggct tccttaatag tggcttgctg ggccgatgag | 2580 |
| ccatggaaac gtccttcttt ttccagcatt atggaaacct tgaaaccaat gactaaacaa | 2640 |
| gcgccacctc aacaaagtcg cacagacacc ctctcggtta tgtgacaatg tgtgtatcat | 2700 |
| aggaatgcct gacgctttgg agggctaagt acggtaccct tcaagagatg tctggcatgt | 2760 |
| ttaaaaccat actccaaaca agcaagcacc tgtgctcgta gccaaatttt ccattgctag | 2820 |
| tagttacaat tttcaagcta agttccttgt accgtgcttc tcaagttttt gtgaacggat | 2880 |
| ggggaagtgt tggaaaactt caactgctag acgattccat caaatttatt ctcagttcat | 2940 |
| aatcatcaaa atgtagagag attataaaaa tgtggatcac ttcatagtcc acaatcaagg | 3000 |
| aagtttctac cttttgcta tggtgatgaa gaaacttcaa ctccatgtca ccctatttca | 3060 |
| cttcacacat tatttgtttg tatatctatt ggtcttacct ttgaggaccg gaccaggaac | 3120 |

```
taattttgta tatactagtg atcagttgtg gatggatgca atcatgtctt cagtcagact    3180
tggtgtttgc tagggaaata tcattgttgt tatttaacag ccacttcaaa cattcaatta    3240
attttcaccg agtctattat tctaaaaaaa aaaaaaaaaa aaaaaa                   3286
```

<210> SEQ ID NO 2
<211> LENGTH: 850
<212> TYPE: PRT
<213> ORGANISM: Cucumis melo
<220> FEATURE:
<221> NAME/KEY: VARIANT
<222> LOCATION: (154)...(154)
<223> OTHER INFORMATION: Xaa = Any Amino Acid

<400> SEQUENCE: 2

```
Met Glu Met Pro Gly Arg Arg Ser Asp Tyr Ser Leu Leu Ser Gln Ile
 1               5                  10                  15

Pro Asp Glu Glu Val Gly Thr Gly Ala Ser Thr Ser Phe Tyr Asp Ser
            20                  25                  30

Val Ala Ala Gly Gly Asn Val Ile Lys Gly Arg Thr Asp Arg Val Phe
        35                  40                  45

Asp Trp Asp Gly Ser Gly Asp His Arg Leu Asn Thr Gln Ala Tyr Arg
    50                  55                  60

Ile Gly Asn Leu Tyr Ser Trp Ile Gly Leu Gln Arg His Ser Ser Gly
65                  70                  75                  80

Ser Ser Tyr Asp Asp Ser Ser Leu Ser Ser Asp Tyr Tyr Ala Pro Thr
                85                  90                  95

Leu Ser Asn Pro Ala Ala Asn Glu Ile Asn Ala Leu Glu Tyr Ile Leu
            100                 105                 110

Asp Asp Asp Phe Arg Val Met Lys Ala Val Gly Ser Gly Ser Ser
        115                 120                 125

Gly Lys Ser Trp Ala Gln Gln Thr Glu Glu Ser Phe Gln Leu Gln Gln
    130                 135                 140

Pro Leu Val Leu Arg Leu Ser Ser Asp Xaa Thr Cys Ala Asp Asp Pro
145                 150                 155                 160

Asn Phe Met Asp Pro Ile Pro Asp Glu Ala Ala Leu Arg Ser Leu Ser
                165                 170                 175

Ile Ser Ala Glu Ala Ile Ser His Arg Phe Trp Val Asn Gly Cys Met
            180                 185                 190

Ser Tyr Leu Glu Lys Val Pro Gly Phe Tyr Leu Ile His Gly Met
        195                 200                 205

Asp Pro Tyr Val Trp Ser Leu Cys Thr Asn Leu Gln Glu Asp Gly Arg
    210                 215                 220

Ile Pro Ser Phe Glu Ser Leu Lys Thr Val Asp Ser Ser Ile Gly Ser
225                 230                 235                 240

Ser Ile Glu Val Val Leu Ile Asp Arg His Ser Asp Ala Ser Leu Lys
                245                 250                 255

Glu Leu Gln Asn Arg Val His Asn Ile Ser Ser Cys Val Thr Thr
            260                 265                 270

Lys Glu Val Ala Asp His Ile Ala Lys Leu Val Cys Asn His Leu Gly
        275                 280                 285

Gly Ser Val Ser Glu Gly Glu Asp Leu Val Ser Ala Trp Lys Glu
    290                 295                 300

Cys Ser Asp Asp Leu Lys Glu Cys Leu Gly Ser Ala Val Ile Pro Leu
305                 310                 315                 320
```

-continued

```
Cys Ser Leu Ser Val Gly Leu Cys Arg His Arg Ala Leu Leu Phe Lys
            325                 330                 335

Val Leu Ala Asp Ser Ile Asp Leu Pro Cys Arg Ile Ala Lys Gly Cys
            340                 345                 350

Lys Tyr Cys Thr Arg Asp Asp Ala Ser Ser Cys Leu Val Arg Phe Gly
            355                 360                 365

Leu Asp Arg Glu Tyr Leu Ile Asp Leu Ile Gly Arg Pro Gly Cys Leu
            370                 375                 380

Cys Gln Pro Asp Ser Leu Leu Asn Gly Pro Ser Ser Ile Ser Ile Ser
385                 390                 395                 400

Ser Pro Leu Arg Phe Pro Arg Leu Lys Pro Ile Glu Ser Thr Ile Asp
            405                 410                 415

Phe Arg Ser Leu Ala Lys Gln Tyr Phe Leu Asp Ser Gln Ser Leu Asn
            420                 425                 430

Leu Val Phe Asp Glu Ala Ser Ser Gly Asn Val Val Ser Gly Lys Asp
            435                 440                 445

Ala Ala Phe Ser Val Tyr Gln Arg Pro Leu Asn Arg Lys Asp Val Asp
450                 455                 460

Gly Lys Thr Ile Val Val Thr Gly Asp Lys Asp Arg Asn Ser Gln Leu
465                 470                 475                 480

Leu Asn Lys Lys Ala Ala Gln Leu Asn Thr Gln Asp Gly Lys Ser Glu
            485                 490                 495

Gln Phe Arg Ser Cys Val Ala Ser Pro Tyr Ser Val Gln Ser Thr Pro
            500                 505                 510

Phe Val Glu Asn Val Val Pro Leu Ser His Ile Ser His Ile Gly Ser
            515                 520                 525

Glu Asp Ser Glu His Leu Leu Ala Leu Ser His Pro Arg Met Asp His
            530                 535                 540

Val Asn Asn Leu Pro Phe Val His Gly Ser Gln Leu Ile Arg Lys Pro
545                 550                 555                 560

Asn Glu Leu Ser Leu Gly Leu Glu Asp Leu Val Ile Pro Trp Thr Asp
            565                 570                 575

Leu Asp Leu Arg Glu Lys Ile Gly Ala Gly Ser Phe Gly Thr Val Tyr
            580                 585                 590

Arg Gly Glu Trp His Gly Ser Asp Val Ala Val Lys Ile Leu Thr Glu
            595                 600                 605

Gln Asp Phe His Pro Glu Arg Val Asn Glu Phe Leu Arg Glu Val Ala
            610                 615                 620

Ile Met Lys Ser Leu Arg His Pro Asn Ile Val Leu Phe Met Gly Ala
625                 630                 635                 640

Val Thr Lys Pro Pro Asn Leu Ser Ile Val Thr Glu Tyr Leu Ser Arg
            645                 650                 655

Gly Ser Leu Tyr Arg Leu Leu His Lys Ser Gly Val Lys Asp Ile Asp
            660                 665                 670

Glu Thr Arg Arg Ile Asn Met Ala Phe Asp Val Ala Lys Gly Met Asn
            675                 680                 685

Tyr Leu His Arg Arg Asp Pro Pro Ile Val His Arg Asp Leu Lys Ser
            690                 695                 700

Pro Asn Leu Leu Val Asp Lys Lys Tyr Thr Val Lys Val Cys Asp Phe
705                 710                 715                 720

Gly Leu Ser Arg Leu Lys Ala Arg Thr Phe Leu Ser Ser Lys Ser Ala
            725                 730                 735

Ala Gly Thr Pro Glu Trp Met Ala Pro Glu Val Leu Arg Asp Glu Pro
```

```
                        740                 745                 750
Ser Asn Glu Lys Ser Asp Val Tyr Ser Phe Gly Val Ile Leu Trp Glu
            755                 760                 765
Leu Ala Thr Leu Gln Gln Pro Trp Cys Asn Leu Asn Pro Ala Gln Val
    770                 775                 780
Val Ala Ala Val Gly Phe Lys Gly Lys Arg Leu Asp Ile Pro Arg Asp
785                 790                 795                 800
Val Asn Pro Lys Leu Ala Ser Leu Ile Val Ala Cys Trp Ala Asp Glu
                805                 810                 815
Pro Trp Lys Arg Pro Ser Phe Ser Ser Ile Met Glu Thr Leu Lys Pro
            820                 825                 830
Met Thr Lys Gln Ala Pro Pro Gln Gln Ser Arg Thr Asp Thr Leu Ser
            835                 840                 845
Val Met
    850
```

<210> SEQ ID NO 3
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 3
caatatttac atccyttggc aattcgac                                        28

<210> SEQ ID NO 4
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 4
cgtgstgakt ggcatggctc kgatgttgc                                       29

<210> SEQ ID NO 5
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 5
atgtttggga tctgctgtga ttcc                                            24

<210> SEQ ID NO 6
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 6
tttggtggct tggtcaccgc accc                                            24

<210> SEQ ID NO 7
<211> LENGTH: 24
<212> TYPE: DNA
<213> ORGANISM: Artificial Sequence
<220> FEATURE:
<223> OTHER INFORMATION: synthetic oligonucleotide

```
<400> SEQUENCE: 7
catgtgttgc ttctccatat agtg                                          24

<210> SEQ ID NO 8
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 8
tcatctatgt ctttgacacc tgac                                          24
```